(12) United States Patent
Tamura et al.

(10) Patent No.: US 7,335,515 B2
(45) Date of Patent: Feb. 26, 2008

(54) (1→3)-β-D-GLUCAN BINDING DOMAIN PROTEIN, MEASURING METHOD USING THE SUBSTANCE AND ASSAY KIT

(75) Inventors: Hiroshi Tamura, Musashi-murayama (JP); Masayuki Tanaka, Nerima-ku (JP); Tatsushi Muta, Fukuoka (JP)

(73) Assignee: Seikagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/600,734

(22) Filed: Nov. 17, 2006

(65) Prior Publication Data

US 2007/0117169 A1    May 24, 2007

Related U.S. Application Data

(62) Division of application No. 10/294,561, filed on Nov. 15, 2002, now abandoned.

(30) Foreign Application Priority Data

Nov. 16, 2001    (JP) .............................. 2001-351943

(51) Int. Cl.
G01N 33/533 (2006.01)
G01N 33/53 (2006.01)
G01N 33/567 (2006.01)

(52) U.S. Cl. ....................... 436/546; 435/7.31; 435/7.2

(58) Field of Classification Search ................ 436/546, 436/800; 435/7.31, 7.2
See application file for complete search history.

(56) References Cited

U.S. PATENT DOCUMENTS 5,795,962 A    8/1998   Iwanaga et al. ............ 530/350
6,156,519 A    12/2000  Tamura et al. .............. 435/7.1

FOREIGN PATENT DOCUMENTS

| EP | 0 598 903 B1 | 6/1994 |
| EP | 0 669 396 A1 | 8/1995 |
| EP | 0 837 330 A2 | 4/1998 |
| WO | WO 9501432   | 1/1995 |
| WO | WO 98/21357 A1 | 5/1998 |

OTHER PUBLICATIONS

Harlow et al. In: Antibodies: A Laboratory Manual. Cold Spring Harbor Laboratory, pp. 217, 354 and 355, 1988.
Houghten et al. Vaccines86, Cold Spring Harbor Laboratory, pp. 21-25, 1986.
Burgess et al. J. Cell Boil. 111: 2129-2138, 1990.
Lazar et al. Mol. Cellular Biol. 8: 1247-1252, 1988.
Bowie et al. Science 247; 1306-1310, 1990.
Seki et al. Biol. Chem. 269: 1370-1374, 1994.

*Primary Examiner*—S. Devi
(74) *Attorney, Agent, or Firm*—Sughrue Mion, PLLC.

(57) ABSTRACT

A (1→3)-β-D-glucan binding protein, a fluorescence-labeled (1→3)-β-D-glucan binding domain protein, a (1→3)-β-D-glucan measuring agent comprising the same, a method for measuring (1→3)-β-D-glucan using the same, and a (1→3)-β-D-glucan assay kit comprising the same.

5 Claims, 3 Drawing Sheets

SEQUENCE LISTING

<160> NUMBER OF SEQ ID NOS: 5

<210> SEQ ID NO 1
<211> LENGTH: 807
<212> TYPE: DNA
<213> ORGANISM: Tachypleus tridentatus
<220> FEATURE:
<221> NAME/KEY: CDS
<222> LOCATION: (1)..(807)
<223> OTHER INFORMATION:

<400> SEQUENCE: 1

```
agt aaa agt tat tct aaa tta att cag gca gaa agt tat ttt gat tcc        48
Ser Lys Ser Tyr Ser Lys Leu Ile Gln Ala Glu Ser Tyr Phe Asp Ser
1               5                   10                  15 tca aaa gta caa ttg gaa gat acc tca gat gta gga ggt ggg aag aat        96
Ser Lys Val Gln Leu Glu Asp Thr Ser Asp Val Gly Gly Gly Lys Asn
            20                  25                  30 gtt aaa tgt gat aat gaa gga gcc tgg atg gct tat aag gat att gat       144
Val Lys Cys Asp Asn Glu Gly Ala Trp Met Ala Tyr Lys Asp Ile Asp
        35                  40                  45 ttc ccc agt tca ggt aat tat cga ata gaa tac aga gta gca agt gaa       192
Phe Pro Ser Ser Gly Asn Tyr Arg Ile Glu Tyr Arg Val Ala Ser Glu
    50                  55                  60 cgt gca gga gga aag ctg tct ctg gat ttg aat gca ggc tct ata gtt       240
Arg Ala Gly Gly Lys Leu Ser Leu Asp Leu Asn Ala Gly Ser Ile Val
65                  70                  75                  80 ctt ggc atg ctg gat gtt cct tca aca gga gga tgg cag aag tgg acc       288
Leu Gly Met Leu Asp Val Pro Ser Thr Gly Gly Trp Gln Lys Trp Thr
                85                  90                  95 acc att tcc cat aca gtg aat gtg gat tca ggt aca tat aac ttg ggg       336
Thr Ile Ser His Thr Val Asn Val Asp Ser Gly Thr Tyr Asn Leu Gly
            100                 105                 110 atc tat gtt caa cga gcc agc tgg aat atc aac tgg ata aag att aca       384
Ile Tyr Val Gln Arg Ala Ser Trp Asn Ile Asn Trp Ile Lys Ile Thr
        115                 120                 125
```

-continued

| | | |
|---|---|---|
| aaa ata cct gaa cag tca aat ttg aat caa ggg cgt cgt aat tct aaa<br>Lys Ile Pro Glu Gln Ser Asn Leu Asn Gln Gly Arg Arg Asn Ser Lys<br>130                                135                        140 | 432 |
| tta att cag gca gaa agt tat ttt agt tac tca gaa gta caa ctg gaa<br>Leu Ile Gln Ala Glu Ser Tyr Phe Ser Tyr Ser Glu Val Gln Leu Glu<br>145                                150                        155                        160 | 480 |
| gat acc tta gat gta gga ggt gga aag aat gtt aaa tgt gat aaa gaa<br>Asp Thr Leu Asp Val Gly Gly Gly Lys Asn Val Lys Cys Asp Lys Glu<br>                          165                        170                        175 | 528 |
| ggg gcc tgg atg gct tac aag gat att gat ttc ccc agt tca gga agt<br>Gly Ala Trp Met Ala Tyr Lys Asp Ile Asp Phe Pro Ser Ser Gly Ser<br>                        180                              185                        190 | 576 |
| tat cga gta gaa tac aga gtg gca agt gaa cgt gca gga gga aag ctg<br>Tyr Arg Val Glu Tyr Arg Val Ala Ser Glu Arg Ala Gly Gly Lys Leu<br>                              195                        200                        205 | 624 |
| tcc cta gat ttg aat gca ggc tct ata gtg ctt ggc atg ctg gat att<br>Ser Leu Asp Leu Asn Ala Gly Ser Ile Val Leu Gly Met Leu Asp Ile<br>210                                215                        220 | 672 |
| cct tca aca gga gga ttg cag aag tgg acc acc att tct cat ata gtg<br>Pro Ser Thr Gly Gly Leu Gln Lys Trp Thr Thr Ile Ser His Ile Val<br>225                                230                        235                        240 | 720 |
| aat gtg gat tta ggt aca tat aac ttg gga att tat gtt caa aaa gcc<br>Asn Val Asp Leu Gly Thr Tyr Asn Leu Gly Ile Tyr Val Gln Lys Ala<br>                        245                        250                        255 | 768 |
| agt tgg aat atc aat tgg att aga att aca aaa gtg tag<br>Ser Trp Asn Ile Asn Trp Ile Arg Ile Thr Lys Val<br>                        260                        265 | 807 |

<210> SEQ ID NO 2
<211> LENGTH: 268
<212> TYPE: PRT
<213> ORGANISM: Tachypleus tridentatus

<400> SEQUENCE: 2

Ser Lys Ser Tyr Ser Lys Leu Ile Gln Ala Glu Ser Tyr Phe Asp Ser
1                 5                     10                 15

Ser Lys Val Gln Leu Glu Asp Thr Ser Asp Val Gly Gly Gly Lys Asn
                 20                   25               30

Val Lys Cys Asp Asn Glu Gly Ala Trp Met Ala Tyr Lys Asp Ile Asp
                 35                   40                 45

Phe Pro Ser Ser Gly Asn Tyr Arg Ile Glu Tyr Arg Val Ala Ser Glu
    50                     55                   60

Arg Ala Gly Gly Lys Leu Ser Leu Asp Leu Asn Ala Gly Ser Ile Val
65                  70                   75                   80

Leu Gly Met Leu Asp Val Pro Ser Thr Gly Gly Trp Gln Lys Trp Thr
                 85                   90                 95

Thr Ile Ser His Thr Val Asn Val Asp Ser Gly Thr Tyr Asn Leu Gly
                100                105             110

Ile Tyr Val Gln Arg Ala Ser Trp Asn Ile Asn Trp Ile Lys Ile Thr
               115                120             125

Lys Ile Pro Glu Gln Ser Asn Leu Asn Gln Gly Arg Arg Asn Ser Lys
        130                  135                140

Leu Ile Gln Ala Glu Ser Tyr Phe Ser Tyr Ser Glu Val Gln Leu Glu
145                 150                155                160

Asp Thr Leu Asp Val Gly Gly Gly Lys Asn Val Lys Cys Asp Lys Glu
                165                170             175

Gly Ala Trp Met Ala Tyr Lys Asp Ile Asp Phe Pro Ser Ser Gly Ser

```
                  180               185               190
Tyr Arg Val Glu Tyr Arg Val Ala Ser Glu Arg Ala Gly Gly Lys Leu
            195               200               205
Ser Leu Asp Leu Asn Ala Gly Ser Ile Val Leu Gly Met Leu Asp Ile
210               215               220
Pro Ser Thr Gly Gly Leu Gln Lys Trp Thr Thr Ile Ser His Ile Val
225               230               235               240
Asn Val Asp Leu Gly Thr Tyr Asn Leu Gly Ile Tyr Val Gln Lys Ala
            245               250               255
Ser Trp Asn Ile Asn Trp Ile Arg Ile Thr Lys Val
            260               265

<210> SEQ ID NO 3
<211> LENGTH: 673
<212> TYPE: PRT
<213> ORGANISM: Tachypleus tridentatus

<400> SEQUENCE: 3

Met Leu Val Leu Leu Cys Cys Val Val Leu His Val Gly Val Ala Arg
1               5                   10                  15
Ile Cys Cys Ser His Glu Pro Lys Trp Gln Leu Val Trp Ser Asp Glu
            20                  25                  30
Phe Thr Asn Gly Ile Ser Ser Asp Trp Glu Phe Glu Met Gly Asn Gly
        35                  40                  45
Leu Asn Gly Trp Gly Asn Asn Glu Leu Gln Tyr Tyr Arg Arg Glu Asn
    50                  55                  60
Ala Gln Val Glu Gly Gly Lys Leu Val Ile Thr Ala Lys Arg Glu Asp
65                  70                  75                  80
Tyr Asp Gly Phe Lys Tyr Thr Ser Ala Arg Leu Lys Thr Gln Phe Asp
                85                  90                  95
Lys Ser Trp Lys Tyr Gly Lys Ile Glu Ala Lys Met Ala Ile Pro Ser
            100                 105                 110
Phe Arg Gly Val Trp Val Met Phe Trp Met Ser Gly Asp Asn Thr Asn
        115                 120                 125
Tyr Val Arg Trp Pro Ser Ser Gly Glu Ile Asp Phe Ile Glu His Arg
    130                 135                 140
Asn Thr Asn Asn Glu Lys Val Arg Gly Thr Ile His Trp Ser Thr Pro
145                 150                 155                 160
Asp Gly Ala His Ala His His Asn Arg Glu Ser Asn Thr Asn Gly Ile
                165                 170                 175
Asp Tyr His Ile Tyr Ser Val Glu Trp Asn Ser Ser Ile Val Lys Trp
            180                 185                 190
Phe Val Asn Gly Asn Gln Tyr Phe Glu Val Lys Ile Gln Gly Gly Val
        195                 200                 205
Asn Gly Lys Ser Ala Phe Arg Asn Lys Val Phe Val Ile Leu Asn Met
    210                 215                 220
Ala Ile Gly Gly Asn Trp Pro Gly Phe Asp Val Ala Asp Glu Ala Phe
225                 230                 235                 240
Pro Ala Lys Met Tyr Ile Asp Tyr Val Arg Val Tyr Gln Asp Ala Ser
                245                 250                 255
Thr Ser Ser Pro Val Gly Asp Thr Ser Leu Asp Gly Tyr Tyr Phe Val
            260                 265                 270
Gln Asn Arg His Ser Glu Leu Tyr Leu Asp Val Thr Asp Ala Ser Asn
        275                 280                 285
```

-continued

```
Glu Asp Gly Ala Phe Leu Gln Gln Trp Ser Tyr Ser Gly Asn Glu Asn
290                 295                 300

Gln Gln Phe Asp Phe Glu His Leu Glu Asn Asn Val Tyr Lys Ile Thr
305                 310                 315                 320

Asn Lys Lys Ser Gly Lys Ser Leu Asp Val Tyr Asn Phe Gly Thr Glu
                325                 330                 335

Asn Gly Val Arg Ile Gln Gln Trp Ser Tyr Gly Gly Ala Arg Asn Gln
                340                 345                 350

Gln Phe Thr Val Gln Ser Val Gly Asp Gly Tyr Tyr Lys Ile Ile Pro
                355                 360                 365

Arg Gly Ser Gly Lys Leu Val Glu Val Ala Asp Phe Ser Lys Asp Ala
370                 375                 380

Gly Gly Lys Ile Gln Gln Trp Ser Asp Asn Gln Leu Ser Gly Gln
385                 390                 395                 400

Trp Lys Leu Ile Lys Ser Lys Ser Tyr Ser Lys Leu Ile Gln Ala Glu
                405                 410                 415

Ser Tyr Phe Asp Ser Ser Lys Val Gln Leu Glu Asp Thr Ser Asp Val
                420                 425                 430

Gly Gly Gly Lys Asn Val Lys Cys Asp Asn Glu Gly Ala Trp Met Ala
                435                 440                 445

Tyr Lys Asp Ile Asp Phe Pro Ser Ser Gly Asn Tyr Arg Ile Glu Tyr
450                 455                 460

Arg Val Ala Ser Glu Arg Ala Gly Gly Lys Leu Ser Leu Asp Leu Asn
465                 470                 475                 480

Ala Gly Ser Ile Val Leu Gly Met Leu Asp Val Pro Ser Thr Gly Gly
                485                 490                 495

Trp Gln Lys Trp Thr Thr Ile Ser His Thr Val Asn Val Asp Ser Gly
                500                 505                 510

Thr Tyr Asn Leu Gly Ile Tyr Val Gln Arg Ala Ser Trp Asn Ile Asn
                515                 520                 525

Trp Ile Lys Ile Thr Lys Ile Pro Glu Gln Ser Asn Leu Asn Gln Gly
                530                 535                 540

Arg Arg Asn Ser Lys Leu Ile Gln Ala Glu Ser Tyr Phe Ser Tyr Ser
545                 550                 555                 560

Glu Val Gln Leu Glu Asp Thr Leu Asp Val Gly Gly Lys Asn Val
                565                 570                 575

Lys Cys Asp Lys Glu Gly Ala Trp Met Ala Tyr Lys Asp Ile Asp Phe
                580                 585                 590

Pro Ser Ser Gly Ser Tyr Arg Val Glu Tyr Arg Val Ala Ser Glu Arg
                595                 600                 605

Ala Gly Gly Lys Leu Ser Leu Asp Leu Asn Ala Gly Ser Ile Val Leu
                610                 615                 620

Gly Met Leu Asp Ile Pro Ser Thr Gly Gly Leu Gln Lys Trp Thr Thr
625                 630                 635                 640

Ile Ser His Ile Val Asn Val Asp Leu Gly Thr Tyr Asn Leu Gly Ile
                645                 650                 655

Tyr Val Gln Lys Ala Ser Trp Asn Ile Asn Trp Ile Arg Ile Thr Lys
                660                 665                 670

Val
```

<210> SEQ ID NO 4
<211> LENGTH: 20
<212> TYPE: DNA
<213> ORGANISM: Artificial Sequence

```
                               -continued

<220> FEATURE:
<223> OTHER INFORMATION: PCR primer

<400> SEQUENCE: 4
agtaaaagtt attctaaatt                                              20

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ctacactttt gtaattctaa                                              20
```

(1→3)-β-D-GLUCAN BINDING DOMAIN PROTEIN, MEASURING METHOD USING THE SUBSTANCE AND ASSAY KIT

This is a divisional Of application Ser. No. 10/294,561 filed Nov. 15, 2002, now abandoned, which claims benefit of Japanese Application No. 2001-351943 filed Nov. 16, 2001. The entire disclosures of the prior application are considered part of the disclosure of the accompanying divisional application and are hereby incorporated by reference.

BACKGROUND OF THE INVENTION

1. Field of the Invention

The present invention relates to a fluorescence-labeled (1→3)-β-D-glucan binding domain protein, a method for measuring (1→3)-β-D-glucan by fluorescence polarization using the fluorescence-labeled (1→3)-β-D-glucan binding domain protein, and an assay kit for carrying out the method.

2. Brief Description of the Background Art

A method for measuring degree of fluorescence polarization (Perrin, *J. Phys. Rad.*, 1: 390-401 (1926)) has been utilized for measuring and analyzing trace amounts of biological substances and the like at high sensitivity using interaction among biological substances.

Examples of the interaction conventionally used include DNA hybridization, binding of a DNA binding protein with DNA, an antigen-antibody reaction, ligand-receptor binding, sugar-lectin binding, and binding of endotoxin and an endotoxin neutralizing protein (WO 98/21357).

On the other hand, a measuring method using a cascade reaction of a serine protease induced by the activation of a *limulus* blood cell extract (amoebocyte lysate) component by (1→3)-β-D-glucan which constitutes a fungal cell wall has been used for the detection of the presence or absence of mycotic infection which causes serious symptoms such as mycoses profundes and the like. However, *limulus* is an extremely valuable biological resource and the capture of *limulus* is regulated in certain regions.

It is known that a (1→3)-β-D-glucan sensitive factor (factor G) which binds to (1→3)-β-D-glucan, contained in *limulus* amoebocyte lysate, binds to (1→3)-β-D-glucan via a (1→3)-β-D-glucan binding domain in the α subunit, and its amino acid sequence and a DNA sequence encoding it have been revealed (WO 95/01432).

However, since changes in the degree of fluorescence polarization cannot be observed as a significant signal when there are no great changes in molecular weight and molecular structure by the binding reaction of a specific binding substance to an objective tested substance and a fluorescence-labeled the substance, it has been considered that the method is not suitable when the molecular weight of the specific binding substance be fluorescence-labeled is too large and the molecular weight of the test substance to be bound thereto is a degree of several thousand Da.

The *limulus* amoebocyte lysate as a valuable biological resource has a limitation in its amount for continuing its use for detecting fungi in the field of medical treatment and environmental hygiene which will continue to expand more and more in the future.

SUMMARY OF THE INVENTION

An object of the present invention is to provide a method for detecting a trace amount of a fungal component, which is identical or superior to the above method for detecting a fungal component by the cascade reaction using *limulus* amoebocyte lysate.

This and other objects of the present invention have been accomplished by a novel method for measuring (1→3)-β-D-glucan.

Furthermore, this and other objects of the present invention have been accomplished by a fluorescence-labeled (1→3)-β-D-glucan binding protein used for the method.

DETAILED DESCRIPTION OF THE INVENTION

Figure 1:
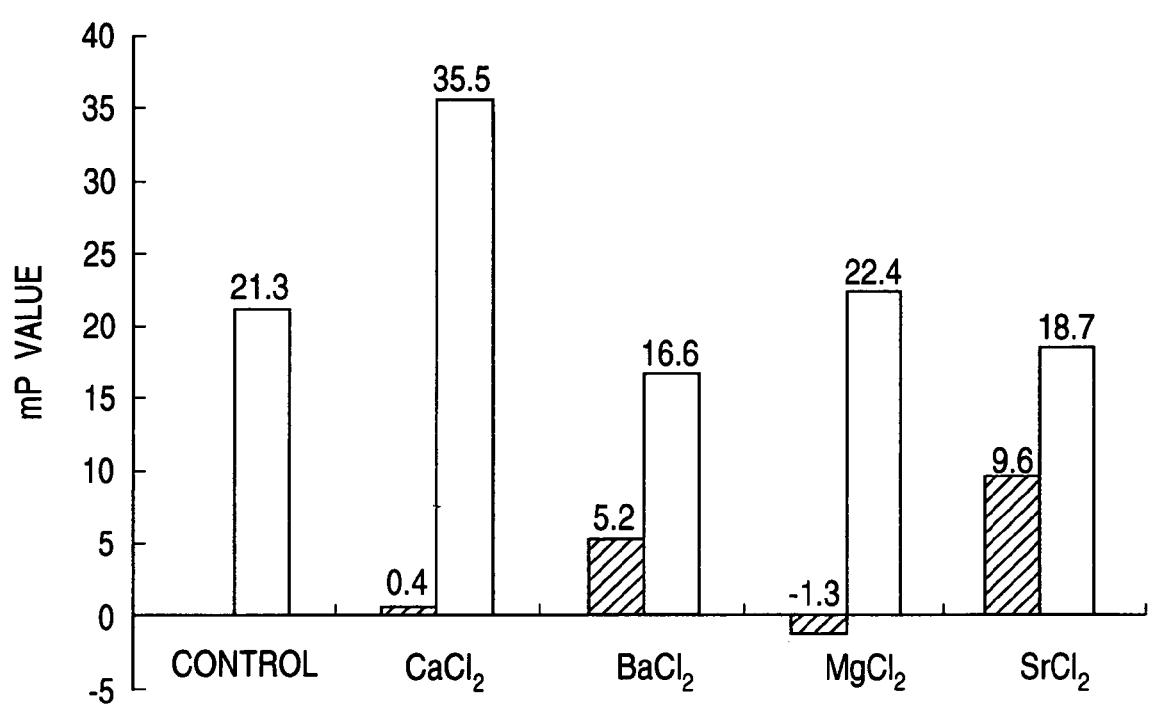
FIG. 1 is a graph showing influence of alkaline earth metal ions on the measurement of (1→3)-β-D-glucan.

The present inventors have conducted intensive studies and found, as a result, that (1→3)-β-D-glucan can be detected markedly precisely when a protein consisting of a (1→3)-β-D-glucan binding domain existing in the α subunit of a (1→3)-β-D-glucan sensitive factor (factor G) derived from *limulus* amoebocyte lysate (herein referred to as "(1→3)-β-D-glucan binding domain protein") is prepared by genetic engineering techniques and labeled with a fluorescence and then (1→3)-β-D-glucan in a sample is measured by a fluorescence polarization method. Furthermore, they have found that the measuring sensitivity is considerably increased when a divalent cation, particularly an alkaline earth metal ion, is allowed to coexist in the reaction solution. Thus, the present invention has been completed.

Specifically, the present invention relates to the following (1) to (13):

(1) A fluorescence-labeled (1→3)-β-D-glucan binding domain protein, which comprises:
a protein comprising the amino acid sequence represented by SEQ ID NO:2; or
a protein comprising an amino acid sequence represented by SEQ ID NO:2 in which a substitution, deletion, insertion, addition or transposition of at least one amino acid residue is made, having a molecular weight of from 10 kDa to 40 kDa, and being capable of binding to (1→3)-β-D-glucan,
wherein a fluorescent material is bound to the protein.

(2) A (1→3)-β-D-glucan measuring agent, which comprises the fluorescence-labeled (1→3)-β-D-glucan binding domain protein according to (1).

(3) The agent according to (2), which further comprises a divalent cation.

(4) The agent according to (3), wherein the divalent cation is an alkaline earth metal ion.

(5) A method for measuring (1→3)-β-D-glucan, which comprises:
binding the fluorescence-labeled (1→3)-β-D-glucan binding domain protein according to (1) to (1→3)-β-D-glucan in a sample;
detecting a change in a degree of fluorescence polarization caused by the binding; and correlating a changed amount of the degree of fluorescence polarization with a concentration of (1→3)-β-D-glucan in the sample.

(6) The method according to (5), wherein the fluorescence-labeled (1→3)-β-D-glucan binding domain protein is bound to the (1→3)-β-D-glucan in the presence of a divalent cation.

(7) A (1→3)-β-D-glucan assay kit, which comprises the fluorescence-labeled (1→3)-β-D-glucan binding domain protein according to (1).

(8) The kit according to (7), which further comprises a divalent cation.

(9) The kit according to (8), wherein the divalent cation is an alkaline earth metal ion.

(10) A protein which consists of:
a protein consisting of the amino acid sequence represented by SEQ ID NO:2; or
a protein consisting of an amino acid sequence represented by SEQ ID NO:2 in which a substitution, deletion, addition or transposition of at least one amino acid residue is made, having a molecular weight of from 10 kDa to 40 kDa, and being capable of binding to (1→3)-β-D-glucan.

(11) A DNA encoding a protein which consists of:
a protein consisting of the amino acid sequence represented by SEQ ID NO:2; or
a protein consisting of an amino acid sequence represented by SEQ ID NO:2 in which a substitution, deletion, addition or transposition of at least one amino acid residue is made, having a molecular weight of from 10 kDa to 40 kDa, and being capable of binding to (1→3)-β-D-glucan.

(12) A DNA which consists of:
a DNA consisting of the nucleotide sequence represented by SEQ ID NO:1; or
a DNA which hybridizes to a nucleotide sequence complementary to the nucleotide sequence represented by SEQ ID NO:1 under stringent conditions, and which encodes a protein having a molecular weight of from 10 kDa to 40 kDa and being capable of binding to (1→3)-β-D-glucan.

(13) A method for detecting mycosis, which comprises:
binding the fluorescence-labeled (1→3)-β-D-glucan binding domain protein according to (1) to (1→3)-β-D-glucan in a sample;
detecting a change in a degree of fluorescence polarization caused by the binding; and
correlating a changed amount of the degree of fluorescence polarization with existence of mycosis.

The present invention is explained below in detail based on embodiments of the present invention.

(1) Substance of the Present Invention

The substance of the present invention is a (1→3)-β-D-glucan binding domain protein to which a fluorescent material is bound.

The (1→3)-β-D-glucan binding domain protein according to the substance of the present invention is a protein which comprises a protein consisting of the amino acid sequence (SEQ ID NO:2) identical to the (1→3)-β-D-glucan binding domain existing in the α subunit of a (1→3)-β-D-glucan sensitive factor (factor G) contained in *limulus* amoebocyte lysate, or a protein consisting of the amino acid sequence represented by SEQ ID NO:2 wherein a substitution, deletion, insertion, addition or transposition of at least one amino acid residue can be made, having a molecular weight of from 10 kDa to 40 kDa, and being capable of binding to (1→3)-β-D-glucan.

Herein, the (1→3)—β-D-glucan binding domain is a protein comprising essentially 268 amino acid residues 406 to 672 in the amino acid sequence of the α subunit of the factor G represented by SEQ ID NO:3.

Accordingly, the (1→3)-β-D-glucan binding domain protein according to the substance of the present invention comprises a protein which consists of the amino acid sequence represented by SEQ ID NO:2, or a protein which consists of an amino acid sequence having high homology therewith, namely an amino acid sequence having a homology of from 70% to 100% (not including 100%), preferably from 80% to 100% (not including 100%), and most preferably from 90% to 100% (not including 100%).

Consequently, a protein comprising the amino acid sequence represented by SEQ ID NO:2 wherein a substitution, deletion, insertion, addition or transposition of at least one amino acid residue is made is included in the (1→3)-β-D-glucan binding domain protein according to the substance of the present invention, so long as the protein has a high homology with the amino acid sequence represented by SEQ ID NO:2 and is capable of binding to (1→3)-β-D-glucan. Herein, the number of an amino acid(s) of the substitution, deletion, insertion, addition or transposition is less than 30%, preferably less than 20%, and most preferably less than 10%, based on the number of total amino acids, more specifically, it is up to 80 amino acids, preferably up to 53 amino acids, and more preferably up to 26 amino acids.

For example, the protein has a molecular weight of from 10 kDa to 40 kDa, preferably from 20 kDa to 40 kDa, more preferably from 25 kDa to 37 kDa, still more preferably from 27 kDa to 32 kDa, and most preferably from 29 kDa to 30 kDa.

Also, a mutant protein in which a substitution, deletion, insertion, addition or transposition of at least one amino acid residue in the protein is made can be obtained by expressing a mutant DNA prepared by introducing a substitution, deletion, insertion, addition or transposition into the nucleotide sequence of a DNA corresponding to the amino acid(s). Such a mutation of DNA can be easily carried out by synthesizing a DNA fragment having a nucleotide sequence containing a sequence moiety where the mutation is to be introduced and having restriction enzyme digestion terminals on both terminals, which is a DNA fragment of a sequence having substitution, deletion, insertion, addition or transposition of at least one nucleotide (the number of nucleotide(s) corresponding to the number of amino acid(s) desired to be mutated) of the DNA fragment, and replacing the DNA fragment for the corresponding nucleotide sequence moiety of un-mutated DNA. Furthermore, a mutation such as substitution, deletion, insertion, addition or transposition can be induced into DNA by a method such as site-directed mutagenesis (Kramer, W. and Frits, H. J., *Meth. In Enzymol.*, 154: 350 (1987), Kunkel, T. A. et al., *Meth. In Enzymol.*, 154: 367 (1987)) or the like.

Also, the amino acid sequence represented by SEQ ID NO:2 is encoded by a DNA comprising the nucleotide sequence represented by SEQ ID NO:1. Also, although several triplets are present corresponding to one amino acid, it is needless to say that a substance which is encoded by a different nucleotide sequence and in which a fluorescent material is bound to a (1→3)-β-D-glucan binding domain protein capable of binding to (1→3)-β-D-glucan is included in the substance of the present invention, so long as it encodes the same amino acid sequence.

In addition, a protein which comprises an amino acid sequence encoded by a DNA comprising a nucleotide sequence which hybridizes to a nucleotide sequence complementary to the nucleotide sequence represented by SEQ ID NO: 1 under stringent conditions and capable of binding to (1→3)-β-D-glucan is also included in the (1→3)-β-D-glucan binding domain protein.

For example, the nucleotide sequence is a DNA which hybridizes to a DNA comprising a nucleotide sequence complementary to the nucleotide sequence represented by SEQ ID NO:1 under stringent conditions, and it is possible to prepare a (1→3)-β-D-glucan binding domain protein by introducing the DNA into an appropriate host (e.g., a procaryotic cell such as *Bacillus subtilis, Escherichia coli* (hereinafter also referred to as "*E. coli*") or the like or a eucaryotic cell such as yeast, mammal cell, insect cell or the like; among these, a procaryotic cell being preferable, and *E. coli* being more preferable) in accordance with a conventional method, carrying out recombination of the gene in accordance with a conventional method and then expressing the introduced gene.

Also, the "stringent conditions" as used herein means conditions in which a sample is incubated at 42° C. for 16 hours in the presence of 50% formamide, 5×SSPE (20× SSPE: aqueous solution of pH 7.4 containing 2.97 M NaCl, 0.2 M $NaH_2PO_4 \cdot H_2O$ and 0.025 M EDTA), 5× Denhardt's solution (100× Denhardt's solution: aqueous solution prepared by dissolving 1 g of FICOLL 400 (manufactured by Pharmacia), 1 g of polyvinyl pyrrolidone (PVP-360: manufactured by Sigma) and 1 g of BSA fraction V (bovine serum albumin: manufactured by Sigma) in 50 ml of water) and 0.5% SDS (sodium dodecyl sulfate), and then washed successively with 1×SSPE containing 0.1% SDS and 0.1×SSPE containing 0.1% SDS at 55° C., or conditions which show functions similar to such conditions in carrying out hybridization of a DNA. It is considered that a DNA which hybridizes to another DNA under such conditions have a homology of at least 70%, for example, a nucleotide sequence having at least 565 nucleotides is common in a DNA consisting of 807 nucleotides.

The fluorescent material in the substance of the present invention is not particularly limited, so long as it is a substance which shows a stable fluorescence. Examples include fluorescein, fluorescein derivatives (fluorescein succinimidyl ester (FS), fluorescein C6 succinimidyl ester (C6 spacer-introduced FS), 5-((aminoethyl)thiouridyl) fluorescein, fluorescein isothiocyanate (FITC), 5-(4,6-dichlorotriazin-2-yl)aminofluorescein, etc.), 4,4-difluoro-4-bora-3a, 4a-diaza-5-indacene-3-propionic acid succinimidyl ester, 6-(((4-(4,4-difluoro-5-(2-thienyl)-4-bora-3a,4a-diaza-5-indacen-3-yl)phenoxy)acetyl)amino)hexanoic acid succinimidyl ester, 4-acetamido-4'-isocyanatostilbene-2,2'-disulfonic acid, 7-amino-4-methylcumarin, 7-amino-4-trimethylcumarin, N-(4-anilino-1-naphthyl)maleimide, dansyl chloride, 4',6-diamidino-2-phenylindole, 4,4'-diisothiocyanatostilben2,2'-disulfonic acid, eosine isothiocyanate, erythrosine B, fluoresamine, fluorescein-5(6)-carboxamidocaproic acid N-hydroxysuccicimide ester, fluorescein-5-isothiocyanate diacetate, 4-methylumbelliferone, o-phthaldialdehyde, Rhodamine B isiothiocyanate, Rhodamine sulfate 101 acid chloride, tetramethyl-Rhodamine isothiocyanate, 2',7'-difluorofluorescein, and the like. Among these, fluorescein and fluorescein derivatives are preferable, and FITC is more preferable.

The binding of the (1→3)-β-D-glucan binding domain protein and a fluorescent material is not limited, so long as the binding is such a degree that the fluorescent material is not released by generally used steps in the detection process, such as washing and the like. Examples include chemical bonds such as hydrogen bond, ionic bond, covalent bond and the like. Binding by a covalent bond is most preferable in view of the particularly strong binding. It is possible to adjust the covalent bond using functional groups such as a carboxyl group, an amino group and the like on side chains and terminals of amino acids contained in the (1→3)-β-D-glucan binding domain protein. The binding may be adjusted using any functional group, so long as it does not inhibit binding of the (1→3)-β-D-glucan binding domain protein to (1→3)-β-D-glucan. Also, among the chemical bonds, a chemical bond which can be formed at a temperature lower than room temperature is preferable particularly from the view point of the stability of (1→3)-β-D-glucan binding domain protein, and a thioamide bond between a thiocyan group of a fluorescent material and an amino group of the (1→3)-β-D-glucan binding domain protein is most preferable because it can be easily formed even at ordinary temperature.

The substance of the present invention can be prepared, e.g., by the following method.

Specifically, the substance of the present invention in which the (1→3)-β-D-glucan binding domain protein and a fluorescent material are bound can be prepared by binding the fluorescent material to the (1→3)-β-D-glucan binding domain protein which has been prepared by genetic engineering techniques, preferably after its purification, under such conditions that the (1→3)-β-D-glucan binding ability of the protein is not inhibited.

The DNA used in preparing the (1→3)-β-D-glucan binding domain protein can be prepared, e.g., by preparing a cDNA library from blood cells (amoebocyte) of *limulus* such ask *Limulus polyphemus, Tachypleus tridentatus, Tachypleus gigas, Tachypleus (Carcinoscorpius) rotundicauda* or the like in the usual way, and amplifying the objective DNA in the library by polymerase chain reaction (hereinafter also referred to as "PCR") using primers of artificially prepared nucleotide sequences represented by SEQ ID NOs:4 and 5. The PCR product can be easily isolated by separating it with molecular weight-dependent separation means such as gel electrophoresis or the like, and recovering a band of about 800 bp using JETSORB (manufactured by GENOMED) or the like by a known method.

In order to insert the thus separated and obtained DNA fragment into a vector suitable for a host cell (e.g., microbial cell, animal cell, insect cell or the like) for expressing the (1→3)-β-D-glucan binding domain protein, restriction enzyme fragments corresponding to the vector are ligated in the usual way. The thus prepared DNA encoding the (1→3)-β-D-glucan binding domain protein can be inserted into the above vector in the usual way, but in order to facilitate purification of the (1→3)-β-D-glucan binding domain protein from a culture mixture of the host cell, it is preferable to use a vector constructed in such a manner that it contains an optional tag (T7 tag, S tag, His tag, HSV tag, pe1B/ompT, KSI, Trx tag, PKA, protein A, FLAG, calmodulin binding domain, glutathione S transferase (GST) or the like) as a homologous expression region. An appropriate combination of the restriction enzyme, vector, tag, host, purification of a fusion protein and cutting of the tag from the fusion protein would be conventionally selected by one of ordinary skill in the art relating to the field of genetic engineering.

For example, when pGEX-2T (manufactured by Pharmacia Biotech) is used as the vector, and GST is used as the tag, a PCR amplification product to which restriction enzyme digestion regions of BamHI and EcoRI are added is digested with the restriction enzymes BamHI and EcoRI, and then the restriction enzyme digestion fragments by BamHI and EcoRI can be inserted into pGEX-2T in the usual way.

Also, it is preferable to insert a gene which expresses resistance to an antibiotic such as ampicillin, neomycin or the like and a peroxidase gene into the vector into which the DNA is to be inserted for facilitating selection of the transfected host cell.

For example, when the vector pGEX-2T having an ampicillin resistance gene is used, a transfected transformant can be selected by introducing the objective gene into E. coli BL21 as the host cell and culturing the E. coli in a medium containing ampicillin.

After growing the thus selected transformant by a respective method, the objective (1→3)-β-D-glucan binding domain protein is prepared from the cultured material (cultured cells, cells, medium or the like).

The substance of the present invention can be prepared from the cultured material obtained by growing the transformant, e.g., by the following method. Also, the term "growing" is a general idea including not only culturing of cells or a microorganism as the transformant but also growth of an animal or insect into which the transformant is introduced. The "cultured material" is a general idea which includes a medium after growth of the transformant, a cultured host cell, a secreted substance and a discharged substance.

When the vector used in the above example and constructed for expressing the objective DNA (a vector constructed in such a manner that pGEX-2T can express a DNA encoding the (1→3)-β-D-glucan binding domain protein and a GST tag as a fusion protein) is used, cultured materials of the host cell (culture supernatant and disrupted product of cultured host cell) can be separated easily by passing them through an affinity column to which GST tag specifically binding-glutathione is bound.

When the (1→3)-β-D-glucan binding domain protein can be cut off from the fusion protein, a method suitable for each tag would be easily selected by one of ordinary skill in the art. When the (1→3)-β-D-glucan binding domain protein is expressed as the above fusion protein with GST tag, the (1→3)-β-D-glucan binding domain protein can be easily cut off, e.g., by reacting it with enterokinase or thrombin. In this case, the (1→3)-β-D-glucan binding domain protein can be eluted alone by allowing the enzyme to react with the fusion protein adhered to a glutathione-binding affinity column.

A fluorescent material can be bound to the (1→3)-β-D-glucan binding domain protein in accordance with a general method. For example, they can be bound by activating an functional group of the fluorescent material or (1→3)-β-D-glucan binding domain protein using an activating reagent such as carbodiimide or the like. However, from the viewpoint of the stability of (1→3)-β-D-glucan binding domain protein, it is preferable to use a fluorescent material which does not require addition of reagents such as a condensing agent, an activating agent and the like, adjustment of pH with acid alkaline or the like and high temperature conditions. A fluorescent material having a thiocyan group is most preferable as such a fluorescent material, and FITC described above as the most preferable example is also most preferable, because the (1→3)-β-D-glucan binding domain protein can be specifically bound through its amino group to FITC through its thiocyan group by a thioamide bond even at 4° C.

Binding of FITC to the (1→3)-β-D-glucan binding domain protein can be carried out, e.g., by dissolving FITC in an aprotic organic solvent (e.g., dialkyl sulfoxide, dialkylformamide, hexaalkylphosphoramide or the like; specifically, diethyl sulfoxide (hereinafter also referred to as "DMSO"), dimethylformamide, hexamethylphosphoramide or the like; and DMSO being particularly preferable), adding the FITC dissolved in the aprotic organic solvent to a buffer in which the (1→3)-β-D-glucan binding domain protein is dissolved, at a pH of from 7 to 9, preferably from 7.5 to 8.5, and then allowed to react for several hours, preferably from 1 to 8 hours, and more preferably from 2 to 6 hours at from 1 to 24° C., preferably from 2 to 10° C.

The thus prepared substance of the present invention can be identified and purified from the reaction solution in accordance with a general molecular weight fractionation method (e.g., gel filtration, gel electrophoresis, ultrafiltration or the like).

(2) Measuring Agent of the Present Invention

The measuring agent of the present invention is a (1→3)-β-D-glucan measuring agent which comprises the substance of the present invention and is used for measuring (1→3)-β-D-glucan by binding it to (1→3)-β-D-glucan in a sample, detecting a change in the degree of fluorescence polarization caused by the binding and correlating the changed amount of the degree of fluorescence polarization to the concentration of (1→3)-β-D-glucan in the sample.

The fluorescent material used in fluorescence labeling and the form for binding the fluorescent material to the protein are similar to those described regarding the substance of the present invention.

The measuring agent of the present invention can be used for the measurement of (1→3)-β-D-glucan concentration in a sample, by binding (1→3)-β-D-glucan in a sample to the substance of the present invention by mixing it with the sample, detecting a change in the degree of fluorescence polarization of the fluorescent material bonded to the protein by the binding and correlating the changed amount to the concentration of (1→3)-β-D-glucan in the sample, namely the measuring method of the present invention described above, and particularly in the field of medical treatment, for example, it can also be used as a diagnostic drug for mycosis or as a kit for diagnosing mycosis.

Furthermore, since binding of the substance of the present invention with (1→3)-β-D-glucan is enhanced by a divalent cation, preferably an alkaline earth metal ion, particularly a calcium ion, the measuring agent of the present invention may also contain these ions.

Moreover, the measuring agent of the present invention may contain a carrier, a diluent, a buffer, a reagent, an additive or the like which is acceptable in the measurement of (1→3)-β-D-glucan.

(3) Measuring Method of the Present Invention

The measuring method of the present invention is a method for measuring (1→3)-β-D-glucan, which comprising binding (1→3)-β-D-glucan in a sample to the substance of the present invention, detecting a change in the degree of fluorescence polarization caused by the binding and correlating the changed amount of the degree of fluorescence polarization to the concentration of (1→3)-β-D-glucan in the sample.

Binding of the substance of the present invention to (1→3)-β-D-glucan in a sample in the measuring method of the present invention is not particularly limited, so long as it is carried out under conditions where they can be bound. However, they are preferably bound particularly at an ionic strength of from 0.01 to 1. Also, they are preferably bound at a pH of from 6.5 to 8.5, particularly from 7.0 to 8.0, because of the ability to carry out the measurement stably. In order to maintain the ionic strength and pH, they are preferably bound in a buffer. Examples of the buffer include phosphate buffered physiological saline (hereinafter also referred to as "PBS"), Tris-HCl buffered physiological saline (hereinafter also referred to as "TBS") and the like, and particularly, TBS is preferably used. TBS is used preferably at a concentration of from 0.1 to 10 times (1×TBS: 20 mM Tris-HCl, 0.15 M NaCl).

Particularly, the sample in the measuring method of the present invention preferably has an ionic strength of particularly from 0.01 to 1. Examples of the sample include blood and urine collected from the living body, a sample collected during a medicament production process, a sample collected using an impinger or the like from the environment such as the air or the like, a sample prepared by dissolving or suspending particles or the like trapped using a filter or the like from the environment, and the like, which may be diluted, if necessary. In each of the samples, a trace amount of (1→3)-β-D-glucan can be measured stably with good reproducibility using the measuring method of the present invention by eliminating factors which inhibit the measurement using generally used method such as deproteinization, ion exchange or the like. Furthermore, the measuring method of the present invention can also be used in detecting mycosis particularly in the medical field.

(4) Assay Kit of the Present Invention

The (1→3)-β-D-glucan assay kit of the present invention comprises the (1→3)-β-D-glucan binding domain protein of the present invention.

Furthermore, since binding of the substance of the present invention with (1→3)-β-D-glucan is enhanced by a divalent cation, preferably an alkaline earth metal ion, particularly a calcium ion, the kit of the present invention may also contain these ions.

Moreover, the kit of the present invention may contain a standard substance, a carrier, a diluent, a buffer, a reagent, an additive or the like which is acceptable in assay.

EXAMPLES

1. Preparation of (1→3)-β-D-glucan Binding Domain Protein (1) Preparation of DNA Encoding (1→3)-β-D-glucan Binding Domain Protein A total RNA was extracted from *Tachypleus tridentatus* amoebocyte, and a cDNA library was prepared from poly (A)⁺ RNA in accordance with a conventional method. The plasmid used was λgt11, and details were based on the cDNA Cloning System λgt11 of AmershamBioscience. In accordance with the method established by Muta et al. (*J. Biol. Chem.*, 268: 1370-1374 (1994)), the factor G and respective subunits (α and β) were purified and the complete amino acid sequence was determined using 477 A Protein Sequencer (manufactured by Applied Biosystems). Oligonucleotide primers were synthesized based on the sequence, and each DNA was amplified 35 cycles by PCR using AmpliTaq (manufactured by PerkinElmer). After labeled with [α-$^{32}$P]dCTP, the objective DNA sequence was confirmed by plaque hybridization using a detection probe prepared from the cDNA library. Using the thus obtained cDNA of the α subunit of factor G as the template and using the primers represented by SEQ ID NOs:4 and 5, the DNA represented by SEQ ID NO:1 encoding the (1→3)-β-D-glucan binding domain protein was prepared by PCR in accordance with a conventional method. A BamHI fragment was ligated to the 5'-end of the DNA obtained as the PCR product, and an EcoRI fragment to the 3'-end, in accordance with a conventional method, and the DNA was inserted into the BamHI-EcoRI region of a pGEX-2T plasmid vector (manufactured by Pharmacia Biotech) which had been treated with BamHI and EcoRI.

(2) Expression and Purification of (1→3)-β-D-glucan Binding Domain Protein

In accordance with the method described in the protocol of GST Gene fusion system (manufactured by Pharmacia Biotech), the plasmid prepared in (1) was expressed using *E. coli* BL21 as the host. Transfection was carried out in accordance with a conventional method using the pGEX-2T plasmid vector prepared in (1). The transfected *E. coli* was cultured in a medium containing ampicillin as an antibiotic. Since pGEX-2T has an ampicillin resistance gene, transformants acquire ampicillin resistance. Accordingly, when *E. coli* is cultured in a medium containing ampicillin, *E. coli* having ampicillin resistance (transfected *E. coli*) alone can be grown selectively. A (1→3)-β-D-glucan binding domain protein-GST fusion protein was purified from the cultured material (culture supernatant and cell debris by ultrasonic disruption) by affinity column chromatography. GLUTATHIONE-SEPHAROSE 4B (manufactured by Pharmacia) was used as the affinity carrier, and the elution was carried out using PBS solution containing 10 µg/ml thrombin.

When the thus eluted (1→3)-β-D-glucan binding domain protein was analyzed by sodium dodecyl sulfate polyacrylamide gel electrophoresis (SDS-PAGE) under reducing conditions in accordance with the method of Laemmli, U. K. et al. (*Nature*, 227, 680-685 (1970)), a single band of 29 kDa in molecular weight was observed, thus confirming that the (1→3)-β-D-glucan binding domain protein prepared by genetic recombination was highly purified.

2. Labeling of (1→3)-β-D-glucan Binding Domain Protein with a Fluorescent Material FITC (manufactured by Wako Pure Chemical Industries) as the fluorescent material was dissolved in dimethyl sulfoxide to give a concentration of 10 mg/ml, the (1→3)-β-D-glucan binding domain protein obtained in the above (1) was added thereto to give a concentration of 1 mg/ml, and the mixed solution was adjusted to have a total volume of 1 ml by adding TBS of pH 8.5. The mixed solution was allowed to react at 24° C. for 4 hours under shading.

After the reaction, the reaction mixture was applied to a SEPHADEX G-25 column (manufactured by Pharmacia) and eluted with 9 ml of PBS at pH 7.4. The eluate from the column was collected, and fractions of 3 to 5 ml were recovered to prepare the substance of the present invention (0.5 to 0.8 mg of protein was detected when determined by the Lowry method).

3. Measuring Method of the Present Invention using the Substance of the Present Invention (1) Effects of Alkaline Earth Metal Salt Into a Borocilicate tube (manufactured by Associates of Cape Cod, Inc.), 1 ml of 0.1×TBS (pH 7.4) was put, 5 µl of a solution which had been prepared by diluting the substance of the present invention with 0.1×TBS (pH 7.4) was added thereto to give a concentration of 100 μg/μl, and the degree of fluorescence polarization was measured as a blank value. In order to examine effects of alkaline earth metal salts, test groups to which one of $CaCl_2$, $BaCl_2$, $MgCl_2$ and $SrCl_2$ were added to give a final concentration of 10 mM and a control group to which no divalent alkaline earth metal salts were added were prepared. After addition of the metal salts, 1 μg of pachyman ((1→3)-β-D-glucan derived from *Poria coccus*, manufactured by Seikagaku Corporation) was added, and changes in the degree of fluorescence polarization before and after the addition of pachyman (mP value) were measured using PolarScan (available from Associates of Cape Cod, Inc.) (FIG. 1).

As a result, it was found that changes in the degree of fluorescence polarization were increased by a factor of about 60% when calcium ion ($CaCl_2$) was added, in comparison with the control.

Figure 2:
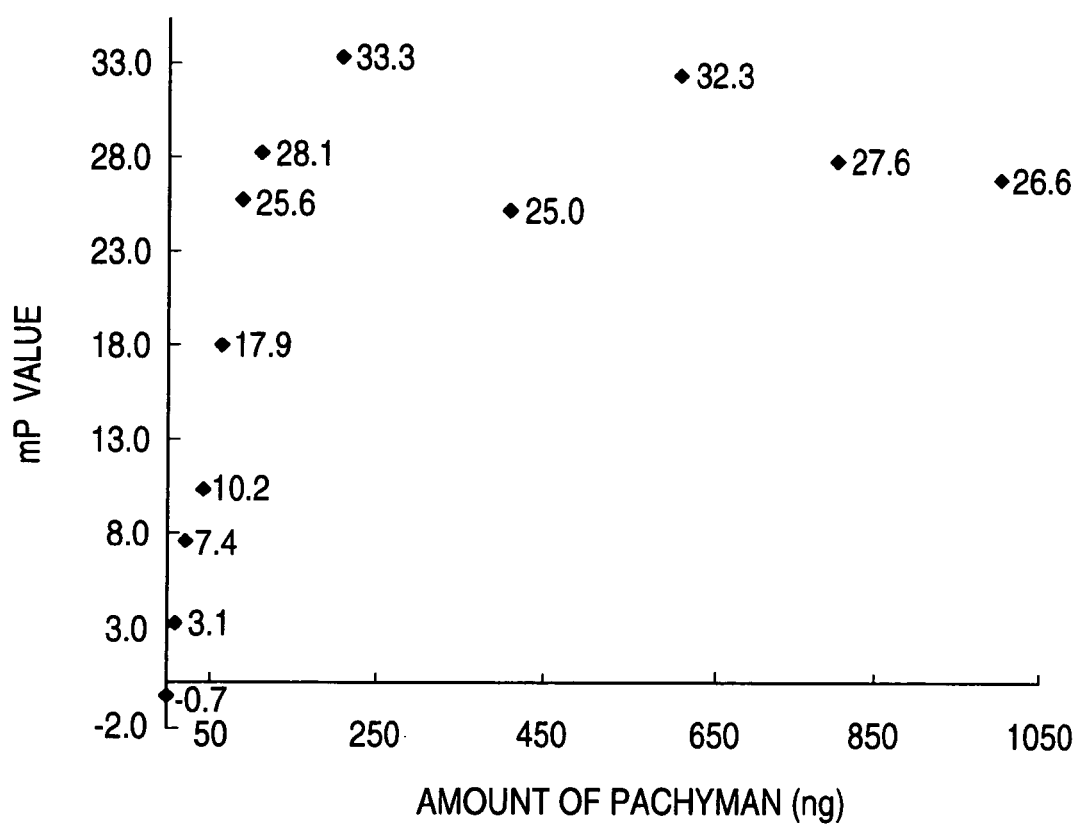
FIG. 2 is a graph showing relationship between the amount of (1→3)-β-D-glucan in samples and changes in the degree of fluorescence polarization.

(2) Examination of Linear Relationship between Concentration of Pachyman and Measured Values Into a Borocilicate tube, 1 ml of 1×TBS (pH 7.4) was put and 10 μl of 1 M $CaCl_2$ was added thereto. To the resulting solution, 5 μl of the substance of the present invention which had been diluted with 1×TBS (pH 7.4) was added to give a concentration of 100 μg/μl, and the degree of fluorescence polarization was measured as a blank value. Thereafter, pachyman was added and changes in the degree of fluorescence polarization before and after the addition of pachyman (mP value) were measured using POLARSCAN (FIG. 2). Amounts added of pachyman were 10 ng, 20 ng, 40 ng, 60 ng, 80 ng, 100 ng, 200 ng, 400 ng, 600 ng, 800 ng and 1,000 ng.

Figure 3:
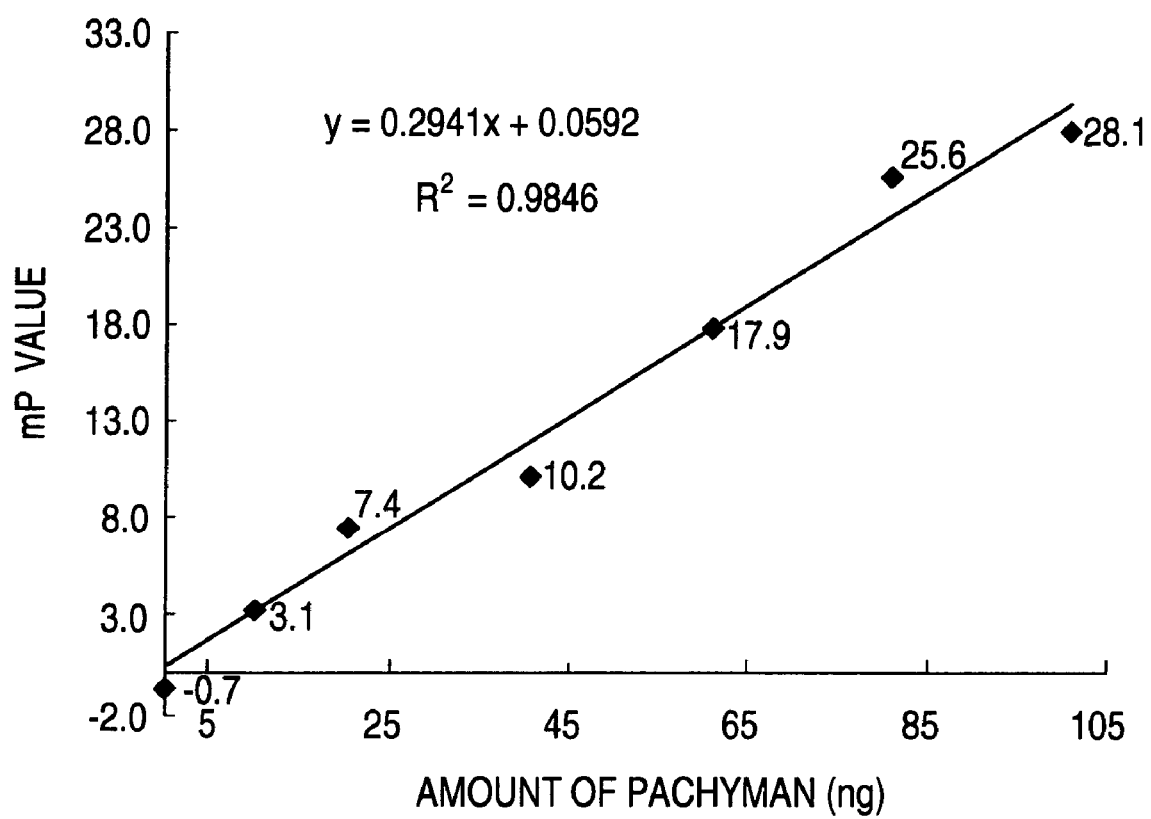
FIG. 3 is a graph showing proportional relationship between the amount of (1→3)-β-D-glucan in samples and the degree of fluorescence polarization.

As a result, it was found that the measured values were almost proportional to the amounts added of pachyman from the group in which no pachyman was added to the groups in which it was added up to 100 ng. Specifically, it was found that a relational expression $Y=0.2941X+0.0592$ ($R^2=0.9846$) is formed between the mP value (Y) and the amounts added of pachyman (X) (FIG. 3).

While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application No. 2001-351943 filed on Nov. 16, 2001, the entire contents of which are incorporated hereinto by reference.

What is claimed is:

1. A method for measuring (1→3)-β-D-glucan concentration in a sample comprising:

binding a fluorescence-labeled (1→3)-β-D-glucan binding domain protein to (1→3)-β-D-glucan in said sample, wherein the protein consists of the amino acid sequence of SEQ ID NO: 2 and is bound to a fluorescent material;

detecting a change in degree of fluorescence polarization caused by the binding; and correlating the change in the degree of fluorescence polarization with the (1→3)-β-D-glucan concentration in the sample.

2. The method according to claim 1, wherein the sample has an ionic strength of from 0.01 to 1.

3. The method according to claim 1, wherein the fluorescence-labeled (1→3)-β-D-glucan binding domain protein is bound to the (1→3)-β-D-glucan in the presence of a divalent cation.

4. The method according to claim 1, wherein the divalent cation is an alkaline earth metal ion.

5. The method according to claim 1, wherein the binding of the fluorescence-labeled (1→3)-β-D-glucan binding domain protein in said sample is carried out in the presence of a buffer.

* * * * *